(12) United States Patent
Nitta et al.

(10) Patent No.: US 7,847,935 B2
(45) Date of Patent: Dec. 7, 2010

(54) METHOD AND APPARATUS FOR GAS CONCENTRATION QUANTITATIVE ANALYSIS

(75) Inventors: Satoshi Nitta, Kameoka (JP); Yoshihiro Osawa, Moriyama (JP)

(73) Assignee: Otsuka Electronics Co., Ltd., Osaka (JP)

( * ) Notice: Subject to any disclaimer, the term of this patent is extended or adjusted under 35 U.S.C. 154(b) by 443 days.

(21) Appl. No.: 12/050,244

(22) Filed: Mar. 18, 2008

(65) Prior Publication Data

US 2008/0231841 A1 Sep. 25, 2008

(30) Foreign Application Priority Data

Mar. 20, 2007 (JP) .............................. 2007-072738

(51) Int. Cl.
*G01J 3/42* (2006.01)
(52) U.S. Cl. ................... 356/320; 356/451; 250/339.07
(58) Field of Classification Search ................. 356/320, 356/73, 451; 250/339.07–339.09
See application file for complete search history.

(56) References Cited

U.S. PATENT DOCUMENTS

2004/0211900 A1* 10/2004 Johnson .................... 250/338.5

FOREIGN PATENT DOCUMENTS

JP 2002-22536 1/2002

* cited by examiner

*Primary Examiner*—Tarifur Chowdhury
*Assistant Examiner*—Abdullahi Nur
(74) *Attorney, Agent, or Firm*—Finnegan, Henderson, Farabow, Garrett & Dunner, L.L.P.

(57) ABSTRACT

An FTIR measurement is conducted on a background gas to obtain a single beam spectrum SB(BG) [C] and a synthetic single beam spectrum SSB(BG)[D], and an FTIR measurement is conducted on a sample gas to obtain a single beam spectrum SB(Samp)[E] and a synthetic single beam spectrum SSB(Samp)[F]. A double synthetic absorbance spectrum DSAbs of the sample gas as expressed by the following formula (Step T9) is calculated to obtain a concentration of a trace component (impurity) contained in the sample gas:

DSAbs = −log[SB(Samp) SSB(BG)/SSB(Samp) SB(BG)]

7 Claims, 10 Drawing Sheets

FIG. 22 ized single beam spectrum SSB(BG) of the background gas, the single beam spectrum SB(Samp) of the sample gas and the synthetic single beam spectrum SSB(Samp) of the sample gas; and obtaining the concentration of the trace component in the sample gas according to this double synthetic absorbance spectrum DSAbs.

According to the above-mentioned method, the four types of single beam spectra SB(Samp), SSB(BG), SSB(Samp) and SB(BG) are obtained, and based on these single beam spectra, the double synthetic absorbance spectrum DSAbs of the sample gas can be calculated. This double synthetic absorbance spectrum DSAbs has a form in which a synthetic absorbance spectrum of the background gas:

$$-\log SB(BG)/SSB(BG) \qquad (3)$$

is subtracted from a synthetic absorbance spectrum SAbs:

$$SAbs = -\log [SB(Samp)/SSB(Samp)] \qquad (2)$$

This synthetic absorbance spectrum (3) of the background gas is the single beam spectrum SB(BG) of the background gas with the synthetic single beam spectrum SSB(BG) of the background gas expressed as the reference.

Accordingly, when the single beam spectrum SB(BG) of the background gas is divided by the synthetic single beam spectrum SSB(BG) of the background gas, the absorbance spectrum (3) of the background gas containing only the trace component can be obtained from which any influence by drift and noise is removed.

On the other hand, the synthetic absorbance spectrum SAbs (Formula (2)) of the sample gas is an absorbance spectrum of the sample gas containing the trace component from which any influence by drift and noise is removed.

Accordingly, the synthetic absorbance spectrum SAbs (Formula (2)) of the sample gas is divided by the absorbance spectrum (Formula (3)) of only the background gas, or the logarithm in the Formula (3) from the logarithm in the Formula (2), the double synthetic absorbance spectrum DSAbs (Formula (1)) can be obtained which represents accurately only the trace component in the sample gas and from which the trace component in the background gas is removed.

Thus, the absorbance spectrum inherent in the trace component can be found, and then the concentration of the trace component can be obtained with the use of a calibration curve.

The gas concentration quantitative analysis method of the present invention may also include a procedure of calculating a normal absorbance spectrum Abs of the sample gas.

Further, the gas concentration quantitative analysis method of the present invention may also include a procedure of calculating a synthetic absorbance spectrum SAbs of the sample gas.

To obtain the concentration of the trace component in the sample gas based on the double synthetic absorbance spectrum DSAbs, a calibration curve may be applied that is data to determine a relationship between an integration values in the measurement wavenumber region of the absorbance spectrum of gas having a known concentration of a trace component, and the concentration of the trace component gas.

A gas concentration quantitative analysis apparatus of the present invention is in accordance with the invention substantially same as that of the gas concentration quantitative analysis method.

These and other features, advantages and operational effects of the present invention will be more fully apparent from the following detailed description set forth below when taken in conjunction with the accompanying drawings.

METHOD AND APPARATUS FOR GAS CONCENTRATION QUANTITATIVE ANALYSIS

BACKGROUND OF THE INVENTION

1. Field of the Invention

The present invention relates to a method and apparatus for quantitatively determining a concentration of a trace component mixed in a gas.

2. Description of Related Art

In a quantitative analysis method of gas concentration using a Fourier transform infrared spectrophotometer, when quantitative analysis is conducted of the concentration of a trace component gas in a sample gas, it is an important task to improve measurement precision. In this connection, it is required to conduct an accurate measurement without any interference by drift and noise.

Accordingly, the following will discuss, for example, a method of calculating an absorbance spectrum Abs of ammonia gas selected as a sample gas and water vapor selected as a trace component gas [1]. There are obtained a single beam spectrum SB(Samp) of the ammonia gas, and a single beam spectrum SB(BG) of background gas (e.g., nitrogen gas) which is not absorbed in a measurement wavenumber region of water vapor. Then, an absorbance spectrum Abs is calculated based on these two types of single beam spectra.

[Patent document 1] Japanese Unexamined Patent Publication 2002-22536.

According to this method, however, it is required to use a background gas having a moisture content removed therefrom by 100%, but it is not possible to obtain a background gas of which moisture content is removed by 100%. Even though nitrogen gas of six-nine (6N) purity is used, moisture content of 0.01 ppm is contained. It is, therefore, difficult to conduct a quantitative analysis of a trace moisture content in the sample gas. Further, the conditions under which the sample gas is measured cannot be made completely identical with those under which the background gas is measured. Accordingly, there remains a drift factor such as temperature variations over time.

SUMMARY OF THE INVENTION

It is an object of the present invention to provide a method and apparatus for quantitatively analyzing a gas concentration, each capable of not only reducing drifts and noise resulting from measurement of a sample gas or background gas, but also accurately measuring a concentration of a trace component gas contained only in the sample gas.

The gas concentration quantitative analysis method according to the present invention comprises the steps of: specifying a sample gas and a measurement wavenumber region thereof; specifying a background gas which is not absorbed in this measurement wavenumber region; conducting an FTIR measurement of a background gas to obtain the single beam spectrum SB(BG) and a synthetic single beam spectrum SSB(BG); conducting an FTIR measurement of the sample gas to obtain a single beam spectrum SB(Samp) and a synthetic single beam spectrum SSB(Samp); calculating a double synthetic absorbance spectrum, DSAbs of the sample gas as expressed by the following formula:

$$DSAbs = -\log [SB(Samp)SSB(BG)/SSB(Samp)SB(BG)] \qquad (1)$$

according to the single beam spectrum SB(BG) of the background gas, the synthetic single beam spectrum SSB

DETAILED DESCRIPTION OF PREFERRED EMBODIMENTS

Figure 1:
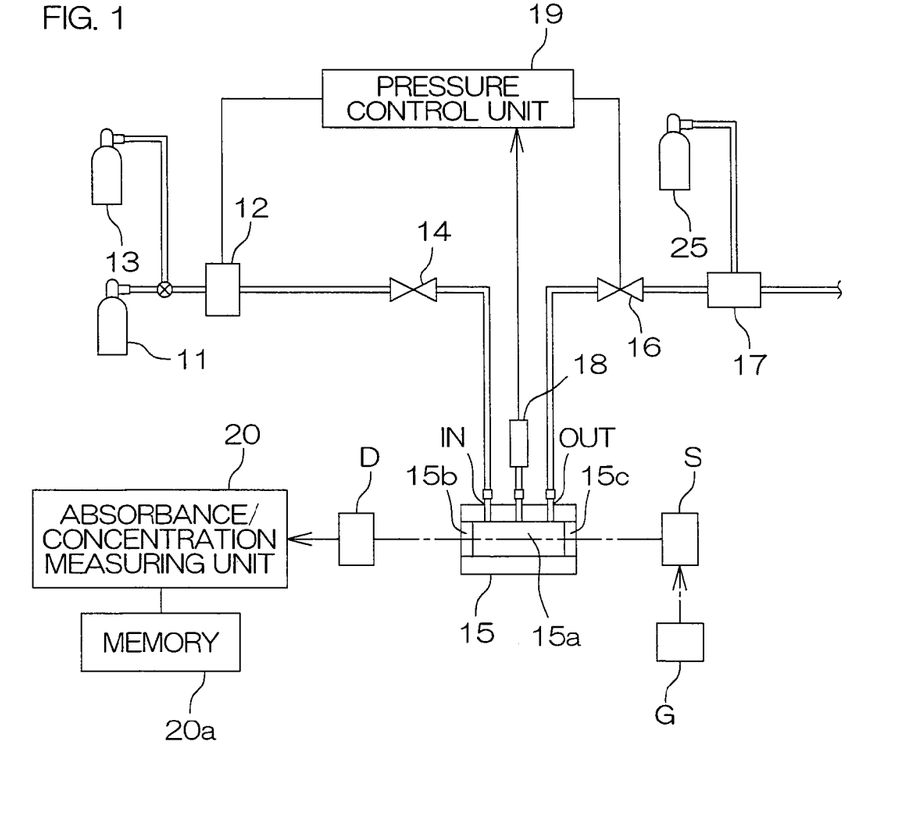
FIG. 1 is a schematic view of a quantitative analysis apparatus for measuring a sample gas.

FIG. 1 is a view illustrating a quantitative analysis apparatus for measuring a sample gas for a quantitative analysis.

In FIG. 1, a sample gas cylinder 11 containing a sample gas and a gas cylinder 13 containing a background gas are set in a gas inlet IN of a gas cell 15 through a mass flow controller 12 for adjusting a gas flow rate and an opening/closing valve 14. The sample gas cylinder 11 and the gas cylinder 13 are switched by a valve mounted on each of the gas cylinders 11 and 13.

On the other hand, an adjusting valve 16 and a vacuum generator 17 (which may be a pressure ejector) for creating a negative pressure are connected to a gas output OUT of the gas cell 15. A high-pressure gas cylinder 25 for air, nitrogen, or the like is connected to the vacuum generator 17.

The gas cell 15 includes a cylindrical cell chamber 15a having a predetermined volume and light transmission windows 15b and 15c provided on both end surfaces of the cell chamber 15a, as shown in FIG. 1. The cell chamber 15a is provided with the gas inlet IN and the gas outlet OUT, and is further provided with a port connected to a pressure transducer 18 for measuring a pressure in the cell chamber 15a.

Respective control lines of the mass flow controller 12, the adjusting valve 16, and a pressure transducer 18 are connected to a pressure controller 19. The pressure controller 19 adjusts the respective flow rates of the sample gas and the background gas and the opening/closing degree of the adjusting valve 16 on the basis of a measured pressure value of the pressure transducer 18 to keep the inside of the gas cell 15 at a predetermined pressure.

The light transmission windows 15b and 15c are made of a material that transmits infrared rays. The material is selected from zinc selenide (ZnSe), calcium fluoride ($CaF_2$), and barium fluoride ($BaF_2$).

The gas cell 15 is surrounded by a heat insulating material such as EPS (expanded polystyrene) to keep at a predetermined temperature easily. The whole gas cell 15, together with an infrared light source G, a spectrometer S, and an infrared detector D, is accommodated in an insulating container (not shown). The inside of the insulating container is kept at a predetermined temperature by a heater or a Peltier device.

An infrared rays generating system may be any system, and can employ a ceramics heater (a surface temperature of 450° C.), for example. A rotating chopper for intercepting at a predetermined period and passing light generated in the infrared light source G may be added.

Furthermore, the spectrometer S for selecting the wavelength of infrared rays is provided. The spectrometer S can employ any configuration. An example is a spectrometer using a concave diffraction grating.

Light that is emitted from the infrared light source G, passes through the spectrometer S, and enters the gas cell 15 through the light transmission window 15c is emitted from the gas cell 15 through the light transmission window 15b, and is detected by the infrared detector D. The infrared detector D includes a DtGs detector (deuterium triglycine sulfate detector), an InAs detector, a CCD (Charge Coupled Device), or the like.

A detection signal of the infrared detector D is analyzed by an absorbance/concentration measuring unit 20. Such an analyzing method will be described later.

A processing function of the pressure controller 19 and the absorbance/concentration measuring unit 20 is realized by a personal computer executing a program recorded on a predetermined medium such as a CD-ROM or a hard disk. A memory 20a connected to the absorbance/concentration measuring unit 20 is realized by a writable/readable file created within a recording medium such as a hard disk.

In the foregoing measuring system, the sample gas and the background gas that are stored in the gas cylinders 11 and 13 are introduced into the gas cell 15. The pressure in the gas cell 15 is measured by the pressure transducer 18. The pressure controller 19 controls the mass flow controller 12 and the adjusting valve 16 such that the measured pressure value reaches a target value. Such feedback control can finally maintain at a desired and predetermined pressure inside of the gas cell 15.

In this state, light is emitted from the infrared light source G for the spectrometer S to spectral scanning. The infrared detector D reads the intensity of the light passed through the gas cell 15. Thus the light intensities of the spectra of the sample gas and the background gas filled in the gas cell 15 can be measured.

Figure 2:
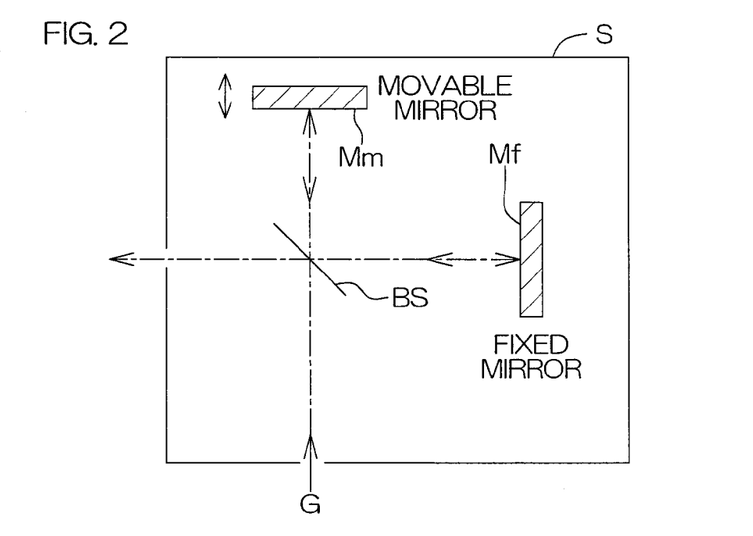
FIG. 2 is an optical path view illustrating the inside structure of an interferometer S.

FIG. 2 is a view illustrating the inside structure of an interferometer S. As shown in FIG. 2, a Michelson interferometer is used as the interferometer S. The following will briefly discuss the measuring principle of the Michelson interferometer.

The "interference" refers to a phenomenon of two overlapping optical waves which intensify or cancel each other. The interferometer is an optical device for generating such interference. Generally, the interferometer is arranged to generate interference by dividing the light emitted from a light source into a plurality of light paths to generate an optical path difference between both light paths, and then by synthesizing again the optical paths.

The interferometer S is made of a semi-transparent mirror (beam splitter BS), one fixed mirror Mf and one movable mirror Mm. The beam splitter BS has a function to pass some of the light emitted from an infrared radiation source G and to reflect the remaining light to divide into two. The light flux incident upon the interferometer S is first divided into two light flux portions by the beam splitter BS. The divided two light flux portions are individually reflected by the fixed mirror Mf and the movable mirror Mm to return to the beam splitter BS, and then synthesized again in the beam splitter BS. The optical path difference between two light flux portions is defined as x.

Suppose that light having a variety of wavenumbers is incident upon the interferometer S. The intensity I(x) of the synthesized light is now expressed as a function of the optical path difference x in the following formula:

$$I(x) = \int B(v)(1 + \cos 2\pi v x) dv \quad (4)$$

wherein $v$ is the wavenumber, $B(v)$ is the wavenumber spectrum, and the integration is conducted in the range from $v=0$ to $v=$infinitely great. This formula (4) includes the DC component and the AC component. When the AC component is expressed in the form of I(x) again, the following formula is obtained:

$$I(x) = \int B(v) \cos 2\pi v x \, dv \quad (5)$$

This formula (5) is referred to as the "interferogram". By conducting a Fourier transformation of this interferogram, the wavenumber spectrum B(v) is obtained.

$$B(v) = \int I(x) \cos 2\pi v x \, dx \quad (6)$$

In principle, the integration is conducted in the range from x=minus infinitely great to x=plus infinitely great. This wavenumber spectrum $B(v)$ is referred to as the "single beam spectrum". A very great value is not necessarily required for the "infinitely great". That is, a sufficiently accurate and good spectrum can be obtained only with a value in the vicinity of x=0 having a high intensity of I(x). Practically, it is sufficient that the integration is conducted in the range from x=0 to the upper limit $x_0$. For example, the upper limit value $x_0$ is set to, for example, 1 cm.

In an integral computation of the formula (6), when a Fourier transformation is conducted with reducing the x point number, a spectrum can be obtained in which the resolution is intentionally lowered. This spectrum is referred to as a synthetic single beam spectrum. This synthetic single beam spectrum is a spectrum having fine concavities and convexities removed based on a trace component (impurity).

Figure 3:
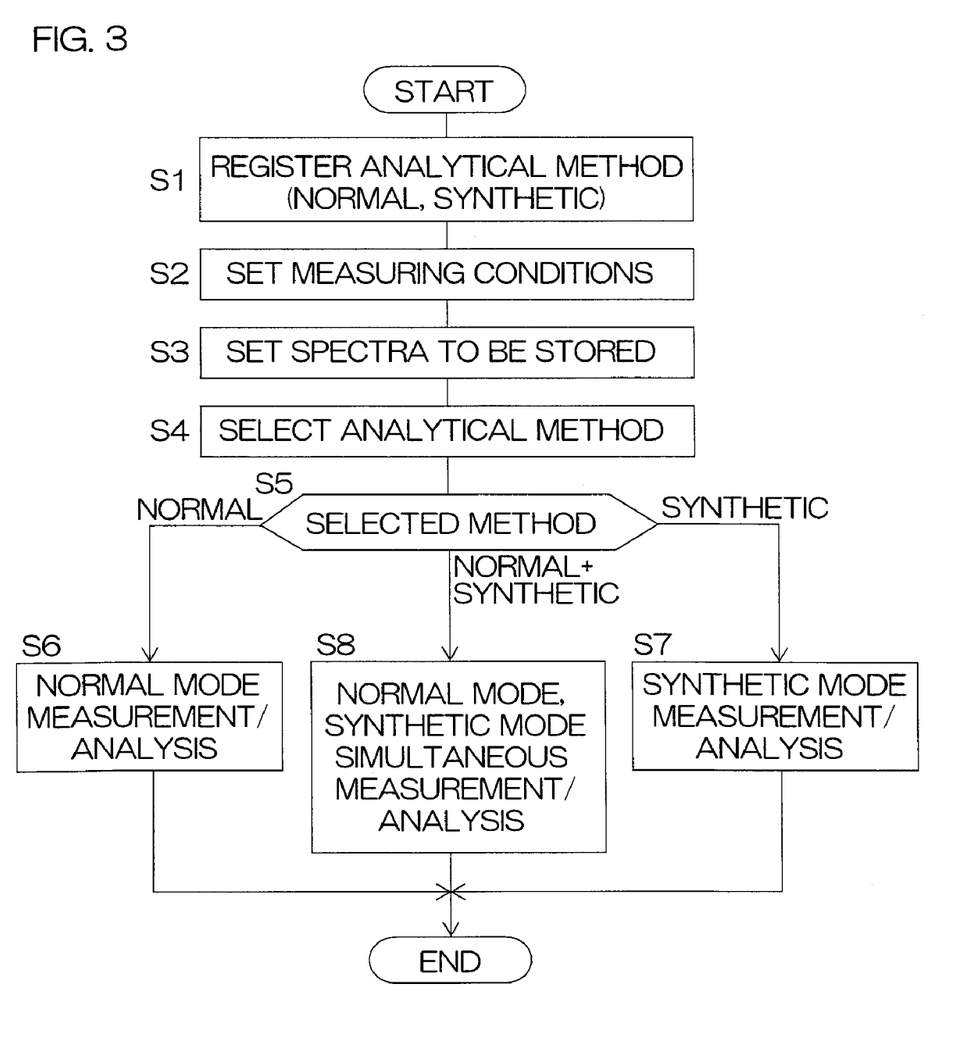
FIG. 3 is a flow chart illustrating the procedure of a gas concentration quantitative analysis of the present invention.

According to the gas concentration quantitative analysis of the present invention, a data processing is conducted in the absorbance spectrum/concentration measuring unit 20 according to the procedure shown in FIG. 3.

In an embodiment of the present invention, nitrogen $N_2$ not absorbed in the measurement wavenumber region of a trace component (impurity) is selected as the background gas, and ammonia gas is selected as the sample gas. The ammonia gas contains water as a trace component (impurity). The nitrogen gas as the background gas also contains water as a trace component (impurity) even in a very small quantity (on 4N to 6N order). The concentration of the water contained in the ammonia gas is quantitatively analyzed.

In the embodiment of the present invention, gas selection is not limited thereto. Other types of gas may be selected as the background gas and the sample gas. For example, an infrared inert gas such as argon gas may be selected as the background gas, and HCL (hydrogen chloride) may be selected as the sample gas.

Referring to FIG. 3, a measurer produces an analytical method of gas concentration quantitative determination to register with the memory 20a (Step S1). Examples of the analytical method include: a "normal mode" in which analysis is conducted with the use of single beam spectra of a background gas and a sample gas; a "synthetic mode" in which analysis is conducted with a single beam spectrum of a sample gas and with a synthetic single beam; and a "double synthetic mode" in which analysis is conducted with the single beam spectra of the background gas and the sample gas and with a synthetic single beam. When the analytical method is registered, calibration curve data are also set and registered that are obtained by measuring the absorbance spectrum of a gas having a known concentration.

In analysis under the normal mode, the types of the background gas and the sample gas are specified and the interferograms of these gases are measured. Then, a Fourier transformation is conducted on these interferograms to obtain the respective single beam spectra. Then, based on these single beam spectra, the absorbance spectrum (referred to as normal absorbance spectrum) of the sample gas is calculated.

In analysis under the synthetic mode, the type of the sample gas is specified and the single beam spectrum of the sample gas is obtained. Then, based on the single beam spectrum thus obtained, the normal absorbance spectrum is obtained, and the synthetic single beam spectrum of the sample gas is obtained. Based on these spectra thus obtained, the absorbance spectrum (referred to as synthetic absorbance spectrum) is calculated.

In the double synthetic mode, the types of the background gas and the sample gas are specified, and the single beam spectrum of the background gas is obtained. Based on the single beam spectrum thus obtained, the normal absorbance spectrum is calculated, and the single beam spectrum of the sample gas is obtained. Then, based on the single beam spectrum thus obtained, the normal absorbance spectrum is calculated, and the synthetic single beam spectrum of the background gas is obtained. Then, based on the synthetic single beam spectrum thus obtained, the synthetic absorbance spectrum is calculated, and the synthetic single beam spectrum of the sample gas is obtained. Then, based on the synthetic single beam spectrum thus obtained, the synthetic absorbance spectrum is calculated. Based on these absorbance spectra, the double synthetic absorbance spectrum is calculated.

Then, the measuring condition is set (Step S2). Examples of the measuring condition include a resolution and a measurement wavenumber region. The resolution is set, for example, in the range from 0.5 $cm^{-1}$ to 2 $cm^{-1}$. The resolution varies dependent on a case of obtaining the synthetic single beam spectrum or the single beam spectrum. Accordingly, the resolution is set for each case. The resolution is coarser in the case of the synthetic single beam spectrum. One or more measurement wavenumber regions are selected in which a high peak for the trace component (impurity) exists. In selection of a plurality of measurement wavenumber regions, selection is made in the order from the domain in which a higher peak for the trace component (impurity) exists in order to improve the measurement sensitivity.

Then, the types of spectra to be stored are set (Step S3). As the spectra to be stored, one or more types are selected out of the interferogram, the single beam spectrum, the normal absorbance spectrum, the synthetic single beam spectrum, the synthetic absorbance spectrum, and the double synthetic absorbance spectrum.

Then, the analytical method is selected (Step S4). The analytical method is to be selected out of the normal mode, the synthetic mode, and the double synthetic mode mentioned earlier.

Figure 4:
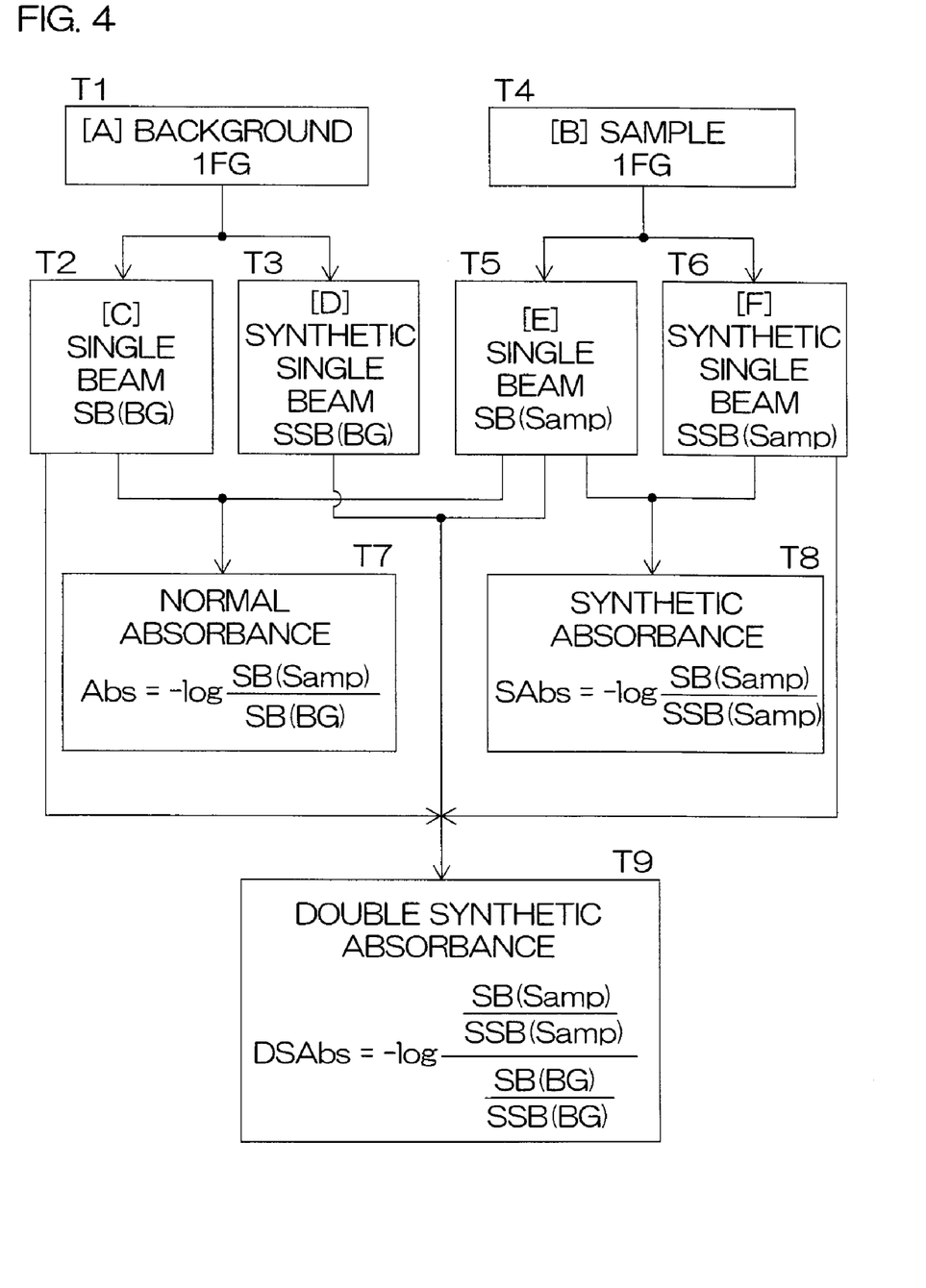
FIG. 4 is a view illustrating the procedure of a method for calculating a normal absorbance spectrum, a synthetic absorbance spectrum and a double synthetic absorbance spectrum.

Then, according to the analytical method thus selected, measurement and analysis are conducted (Steps S6 to S8). Referring to FIG. 4, the measurement and analysis will be discussed in detail in the following.

FIG. 4 shows the procedure of how to obtain a normal absorbance spectrum, a synthetic absorbance spectrum and a double synthetic absorbance spectrum which is characteristic to the present invention.

In the normal mode measurement and analysis, an FTIR measurement is conducted on a background gas to obtain an interferogram (Step T1), and a single beam spectrum SB(BG) is obtained (Step T2). Then, an FTIR measurement is conducted on a sample gas to obtain an interferogram (Step T4), and a single beam spectrum SB(Samp) is obtained (Step T5). Then, the single beam spectrum SB(Samp) is divided by the single beam spectrum SB(BG) to obtain a normal absorbance spectrum Abs (Step T7).

$$\text{Abs} = -\log \text{SB(Samp)}/\text{SB(BG)} \quad (7)$$

This normal absorbance spectrum expresses the single beam spectrum of the sample gas with the single beam spectrum of the background gas serving as the reference.

There is a plurality of sample gases to be quantitatively measured for a trace component (impurity) gas therein. These sample gases are measured within one day. Accordingly, a sample gas measurement is conducted several times a day. However, a background-gas measurement is conducted generally once a day. Accordingly, when the sample gas is quantitatively measured for the trace component (impurity) gas contained in the sample gas based on the normal absorbance spectrum (Formula (7)), it is difficult to remove the interference by temperature variations or the like (drift).

In the synthetic mode measurement and analysis, an FTIR measurement is conducted on the sample gas to obtain an interferogram (Step T4), and a single beam spectrum SB(Samp) is obtained (Step T5). Then, an FTIR measurement is conducted on a sample gas to obtain an interferogram, and a synthetic single beam spectrum SSB(Samp) is obtained (Step T6). Then, the single beam spectrum SB(Samp) is divided by the synthetic single beam spectrum SSB(Samp) to obtain a synthetic absorbance spectrum SAbs (Step T8):

$$\text{SAbs} = -\log \text{SB(Samp)}/\text{SSB(Samp)} \quad (8)$$

This synthetic absorbance spectrum SAbs expresses the single beam spectrum SB(Samp) of the sample gas containing a trace component (impurity) with the synthetic single beam spectrum SSB(Samp) of the sample gas serving as the reference. As mentioned earlier, the synthetic single beam spectrum SSB (Samp) is a spectrum with fine concavities and convexities based on the trace component (impurity) removed. The synthetic single beam spectrum SSB(Samp) and the single beam spectrum SB(Samp) are obtained based on the same data that are measured simultaneously. Accordingly, the synthetic single beam spectrum SSB(Samp) has a function of removing the interference due to a fluctuation component such as temperature. Thus, for the sample gas containing a trace component (impurity), the absorbance spectrum can be obtained from which any influence by noise or drift is removed and contains the trace component (impurity).

In the double synthetic mode measurement and analysis, an interferogram of a background gas is obtained (Step T1), and a single beam spectrum SB(BG) is obtained (Step T2). Then, based on the interferogram of the background gas, a synthetic single beam spectrum SSB(BG) is obtained (Step T3). Then, an interferogram of a sample gas is obtained (Step T4), and a single beam spectrum SB(Samp) is obtained (Step T5). Then, based on the interferogram of the sample gas, a synthetic single beam spectrum SSB(Samp) is obtained (Step T6).

Then, according to the single beam spectrum SB(BG) of the background gas, the synthetic single beam spectrum SSB(BG) of the background gas, the single beam spectrum SB(Samp) of the sample gas and the synthetic single beam spectrum SSB(Samp) of the sample gas, the double synthetic absorbance spectrum DSAbs is calculated (Step T9):

$$\text{DSAbs} = -\log [\text{SB(Samp)}\text{SSB(BG)}/\text{SSB(Samp)}\text{SB(BG)}] = -[\log \text{SB(Samp)}/\text{SSB(Samp)} - \log \text{SB(BG)}/\text{SSB(BG)}] \quad (9)$$

As understood from the function form (9) of this double synthetic absorbance spectrum, the spectrum DSAbs is expressed in the form in which the synthetic absorbance spectrum of the background gas:

$$-\log \text{SB(BG)}/\text{SSB(BG)} \quad (10)$$

is subtracted from the synthetic absorbance spectrum SAbs (Formula(8)).

This background gas synthetic absorbance spectrum (Formula (10)) is the background gas single beam spectrum SB(BG) with the background gas synthetic single beam spectrum SSB(BG) expressed as the reference. The single beam spectrum SB (BG) of the background gas is divided by the synthetic single beam spectrum SSB(BG) of the background gas, the background gas absorbance spectrum formula (10) can be obtained from which any influence by a fluctuation component such as temperature is removed.

As mentioned earlier, the background gas contains a trace component (impurity) even in a very small quantity (4N to 6N order).

Then, the synthetic absorbance spectrum SAbs (Formula (8)) of the sample gas is divided by the absorbance spectrum (Formula (10)) of only the background gas, that is, the logarithm in the Formula (10) is subtracted from the logarithm in the Formula (8), the double synthetic absorbance spectrum DSAbs (Formula (9)) can be obtained containing only the trace component (impurity) of the sample gas from which the trace component (impurity) in the background gas is removed.

Thus, it is possible to find the accurate absorbance spectrum of the trace component (impurity) contained in the sample gas.

Then, the absorbance spectrum of the trace component (impurity) is applied to a calibration curve previously prepared under the condition of the same temperature, the same pressure and the like to obtain the concentration of the trace component (impurity).

Here, the "calibration curve" is data which determine the relationship between the gas concentration and the integration value of the absorbance spectrum in the measurement wavenumber region. The calibration curve is prepared using a gas in which the concentration of the trace component is known, and an absorbance spectrum of this gas. The concentration of the trace component gas is changed to measure the absorbance spectrum of the gas. The concentration of the trace component gas is assigned to the axis of abscissa, while the "integration value of the absorbance spectrum in the measurement wavenumber region" is assigned to the axis of ordinate. Data are then plotted and the curve form is determined with the use of the method of least squares. The data in the curve form are stored in the memory 20a of the absorbance/concentration measuring unit 20.

As thus discussed in the foregoing, the concentration of a trace component (impurity) contained in the sample gas, and having unknown concentration can be quantitatively obtained with the use of the calibration curve.

EXAMPLE 1

With nitrogen gas selected as a background gas and ammonia gas as a sample gas, an interferogram, a single beam spectrum, a synthetic single beam spectrum and an absorbance spectrum were measured. The results are now discussed with reference to the graphs (FIGS. 5 to 13). The symbols, [A], [B] and the like in the following description are corresponding to the reference symbols in FIG. 4. The resolution was selected to be 2 cm$^{-1}$ for a single beam spectrum, and 8 cm$^{-1}$ for a synthetic single beam spectrum, and the measurement wavenumber region was selected to be in the range from 3,000 cm$^{-1}$ (3.3 μm) to 4,500 cm$^{-1}$ (2.2 μm).

Figure 5:
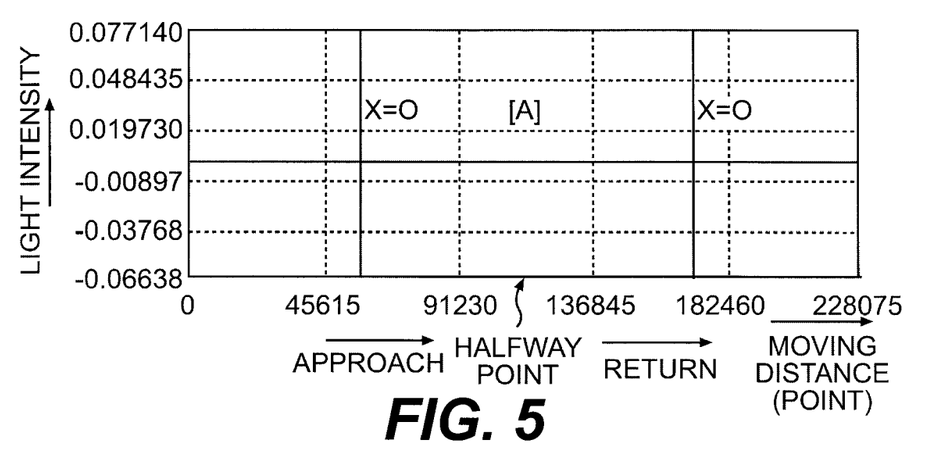
FIG. 5 shows a graph illustrating the interferogram [A] of a background gas according to Example 1.

FIG. 5 shows the interferogram [A] of the background gas. The axis of abscissa expresses the moving distance of the mirror Mm (unit: point. In this Example, 1 point corresponds to 1.25 μm) . The mirror Mm is arranged to reciprocate. However, the graph separately represents the data on approach to the halfway point at the maximum moving distance, and on return from the halfway point. Each point at the optical difference x=0 is expressed by a vertical line.

Figure 6:
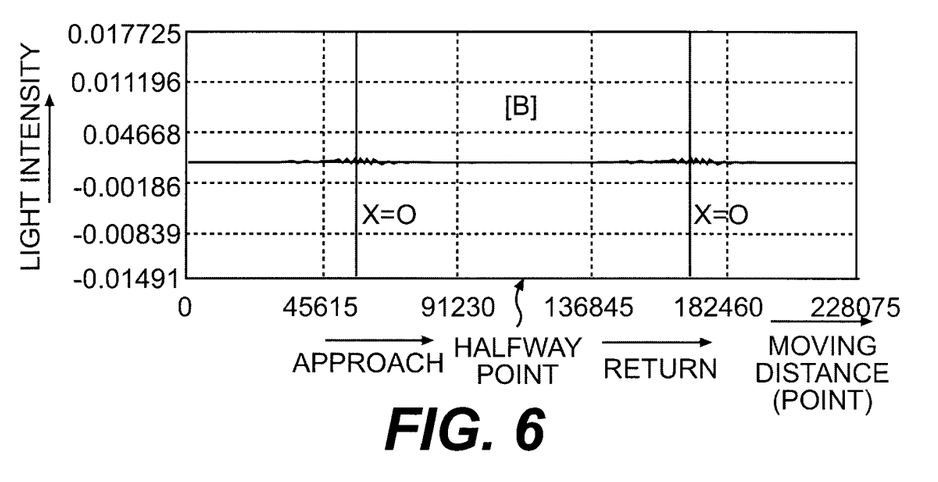
FIG. 6 shows a graph illustrating the interferogram [B] of a sample gas according to Example 1.

FIG. 6 shows the interferogram [B] of the sample gas. As compared with FIG. 5, a signal of water which is the trace component (impurity) appears in the vicinity of each point at x=0.

Figure 7:
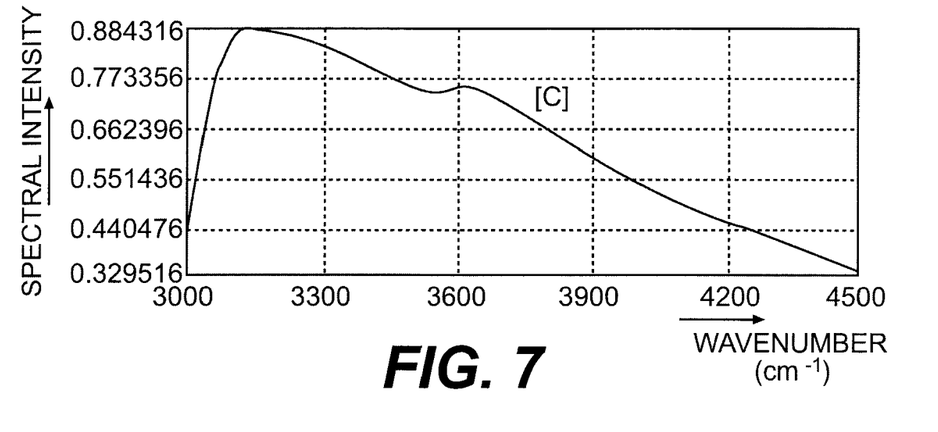
FIG. 7 shows a graph illustrating the single beam spectrum [C] of the background gas according to Example 1.

FIG. 7 shows the single beam spectrum [C] of the background gas. This was obtained by conducting a Fourier transformation of the interferogram [A] of the background gas.

Figure 8:
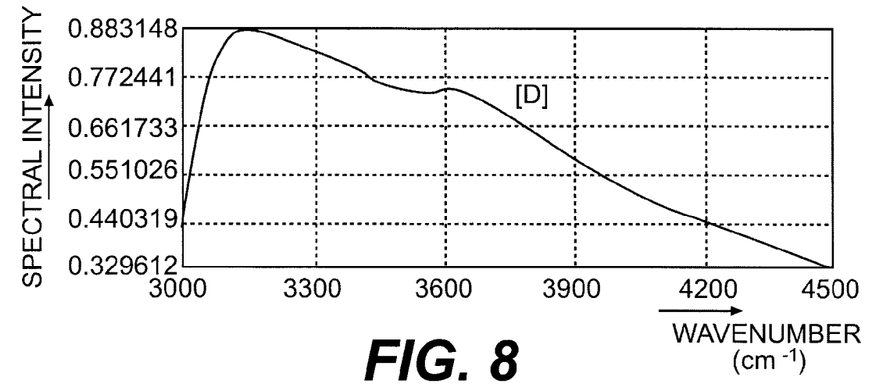
FIG. 8 shows a graph illustrating the synthetic single beam spectrum [D] of the background gas according to Example 1.

FIG. 8 shows the synthetic single beam spectrum [D] of the background gas. This was obtained by conducting a Fourier transformation on the interferogram [A] of the background gas with a lowered resolution.

Figure 9:
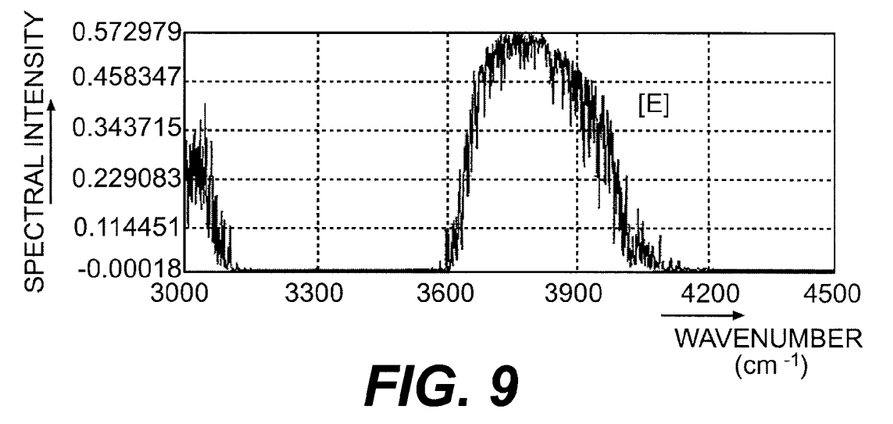
FIG. 9 shows a graph illustrating the single beam spectrum [E] of the sample gas according to Example 1.

FIG. 9 shows the single beam spectrum [E] of the sample gas. This was obtained by conducting a Fourier transformation on the interferogram [B] of the sample gas.

Figure 10:
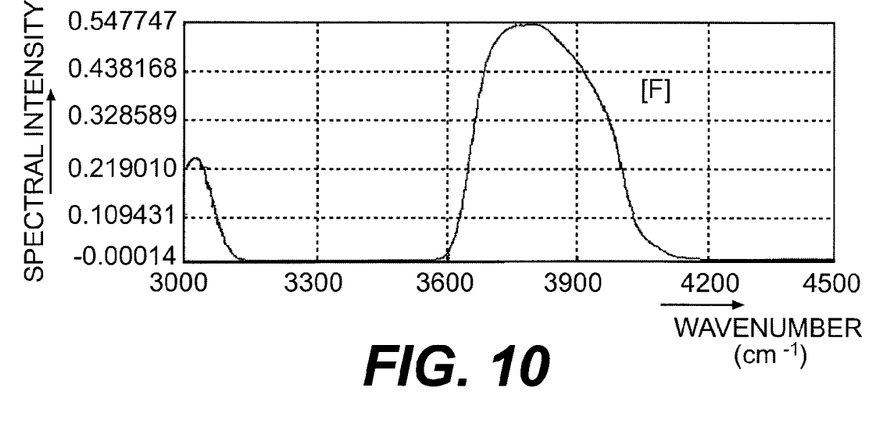
FIG. 10 shows a graph illustrating the synthetic single beam spectrum [F] of the sample gas according to Example 1.

FIG. 10 shows the synthetic single beam spectrum [F] of the sample gas. This was obtained by conducting a Fourier transformation on the interferogram [B] of the sample gas with a lowered resolution.

Figure 11:
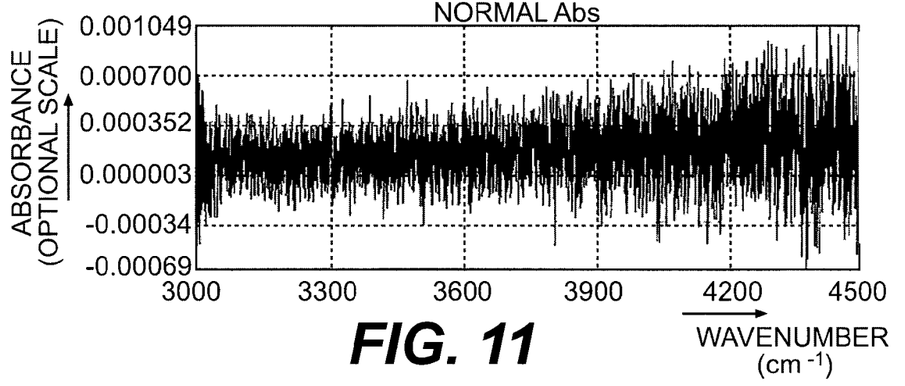
FIG. 11 shows a graph illustrating the normal absorbance spectrum of the sample gas according to Example 1.

FIG. 11 shows a graph of the normal absorbance spectrum Abs of the sample gas. The data in this graph were obtained by calculating the data of the graph [C] in FIG. 7 and the data of the graph [E] in FIG. 9. According to the graph in FIG. 11, the average or DC component of the normal absorbance spectra Abs varies along the axis of abscissa. Thus, a drift influence is observed.

Figure 12:
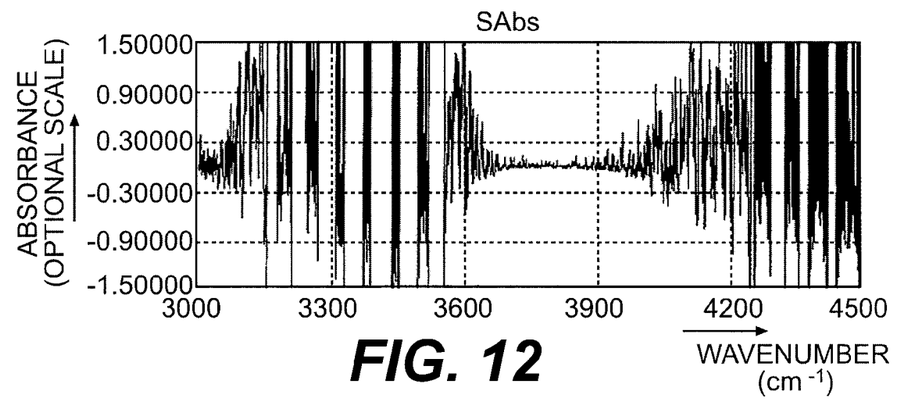
FIG. 12 shows a graph illustrating the synthetic absorbance spectrum of the sample gas according to Example 1.

FIG. 12 shows a graph of the synthetic absorbance spectrum SAbs of the sample gas. The data in this graph were obtained by calculating the data of the graph [E] in FIG. 9 and the data of the graph [F] in FIG. 10. According to the graph in FIG. 12, the average or DC component of the normal absorbance spectra Abs do not vary along the axis of abscissa. Thus, a drift influence is eliminated.

Figure 13:
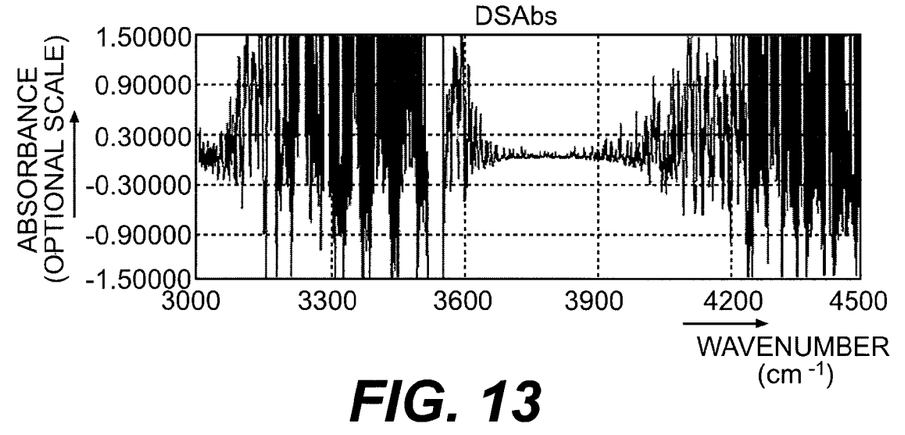
FIG. 13 shows a graph illustrating the double synthetic absorbance spectrum of the sample gas according to Example 1.

FIG. 13 shows a graph of the double synthetic absorbance spectrum DSAbs of the sample gas. The data in this graph were obtained by calculating the data of the graph [C] in FIG. 7, the data of the graph [D] in FIG. 8, the data of the graph [E] in FIG. 9 and the data of the graph [F] in FIG. 10. In FIGS. 12 and 13, the wavenumber region actually used in the analysis is in the vicinity of 3659 cm$^{-1}$ to 3681 cm$^{-1}$. In this range of wavenumber region, the noise was lowered by conducting a calibration with the background gas.

EXAMPLE 2

With nitrogen gas selected as a background gas and air as a sample gas, an interferogram, a single beam spectrum, a synthetic single beam spectrum and a normal absorbance spectrum were measured. The results are now discussed with reference to the graphs (FIGS. 14 to 22). The symbols, [A], [B] and the like in the following description are corresponding to the reference symbols in FIG. 4. The resolution was selected to be 2 cm$^{-1}$ for measurement of a single beam spectrum, and 8 cm$^{-1}$ for measurement of a synthetic single beam spectrum, and the measurement wavenumber region was selected to be in the range of 600 cm$^{-1}$ (3.3 μm) ~4,500 cm$^{-1}$ (2.2 μm).

Figure 14:
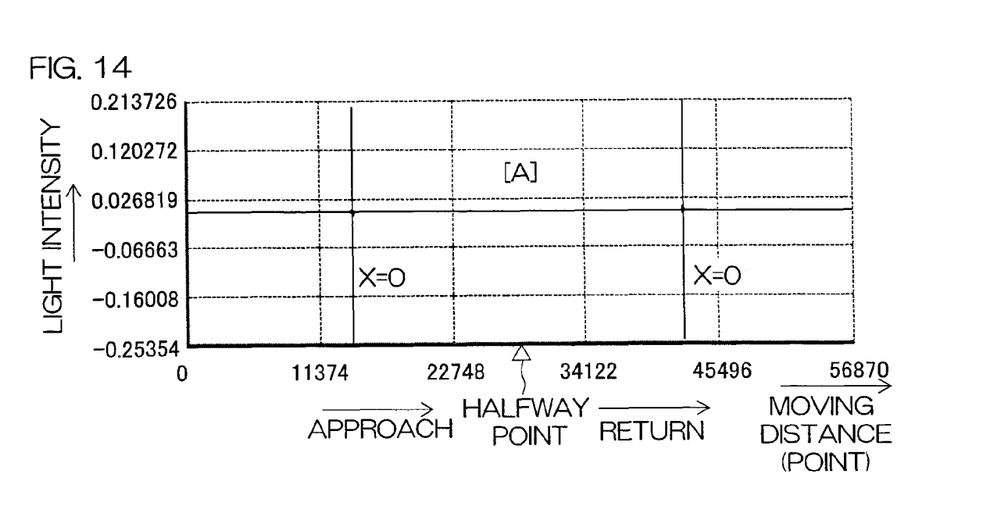
FIG. 14 shows a graph illustrating the interferogram [A] of a background gas according to Example 2.

FIG. 14 shows the interferogram [A] of the background gas. The axis of abscissa expresses the moving distance of the mirror Mm (unit: point. In this Example, 1 point corresponds to 1.25 μm) . The mirror Mm is arranged to reciprocate. However, the graph separately represents the data on approach to the halfway point at the maximum moving distance, and on return from the halfway point. Each point at the optical difference x=0 is expressed by a vertical line.

Figure 15:
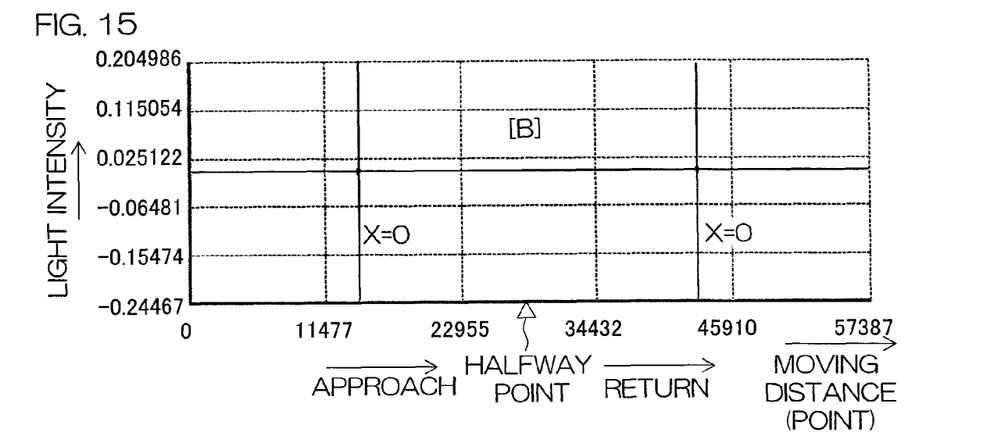
FIG. 15 shows a graph illustrating the interferogram [B] of a sample gas according to Example 2.

FIG. 15 shows the interferogram [B] of the sample gas.

Figure 16:
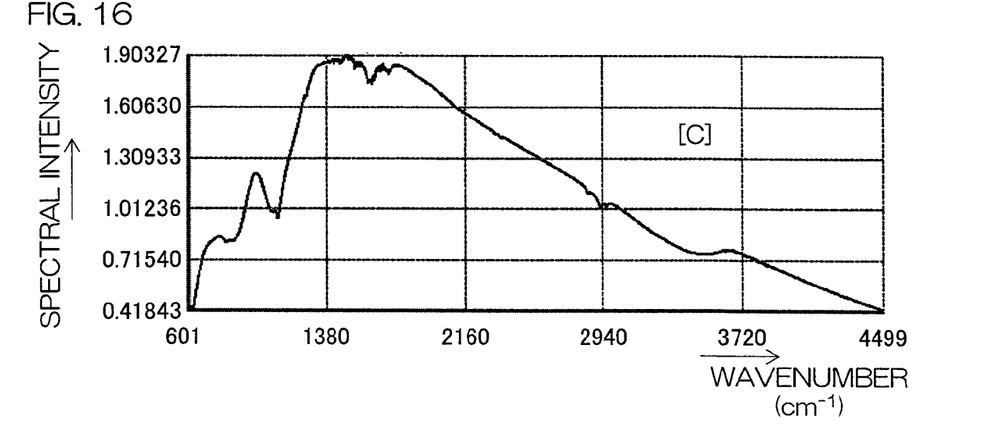
FIG. 16 shows a graph illustrating the single beam spectrum [C] of the background gas according to Example 2.

FIG. 16 shows the single beam spectrum [C] of the background gas. This was obtained by conducting a Fourier transformation on the interferogram [A] of the background gas. In the vicinity of 1,500 cm$^{-1}$, there appears the spectrum of carbon dioxide and water which are the trace components (impurity) . This is because carbon dioxide and water are contained even in a very small quantity (4N-6N order) in the nitrogen gas serving as the background gas.

Figure 17:
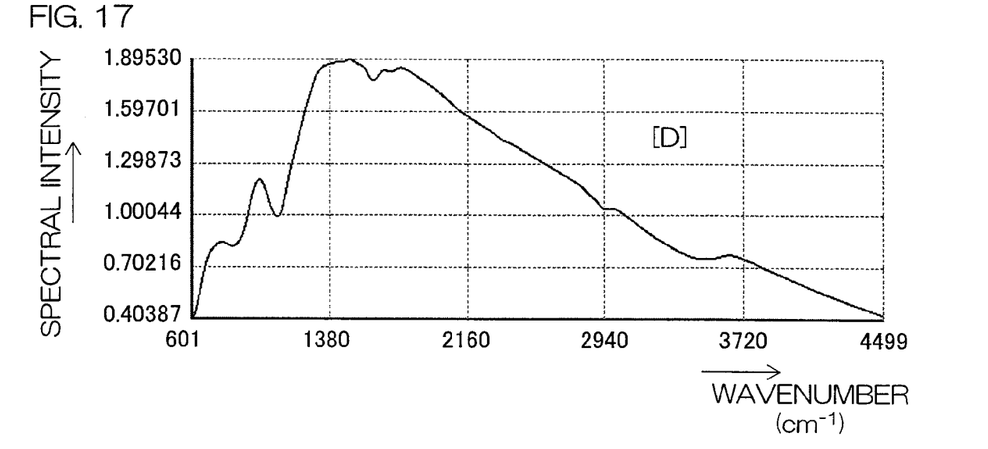
FIG. 17 shows a graph illustrating the synthetic single beam spectrum [D] of the background gas according to Example 2.

FIG. 17 shows the synthetic single beam spectrum [D] of the background gas. This was obtained by conducting a Fourier transformation on the interferogram [A] of the background gas with a lowered resolution. As compared with FIG. 16, there disappears the signal of nitrogen gas and water which are the trace components (impurity).

Figure 18:
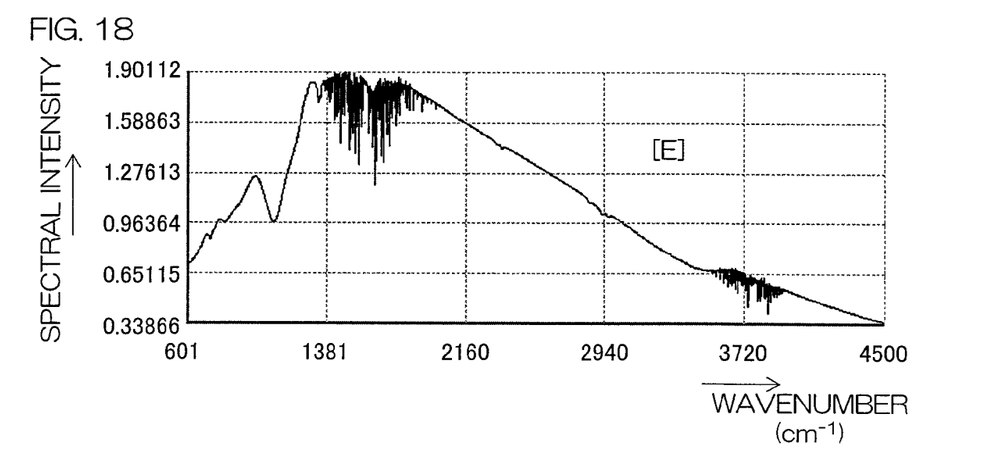
FIG. 18 shows a graph illustrating the single beam spectrum [E] of the sample gas according to Example 2.

FIG. 18 shows the single beam spectrum [E] of the sample gas. This was obtained by conducting a Fourier transformation on the interferogram [B] of the sample gas. Due to the Fourier transformation, there appears the absorption by $CO_2$ or moisture content in the air.

Figure 19:
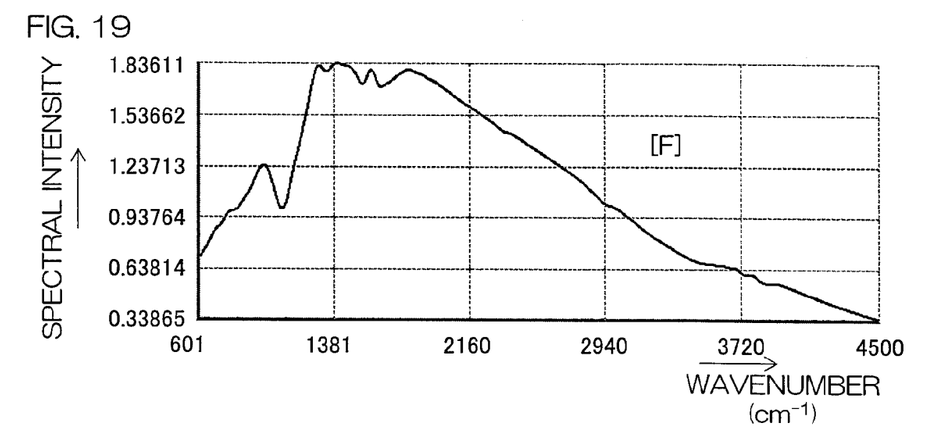
FIG. 19 shows a graph illustrating the synthetic single beam spectrum [F] of the sample gas according to Example 2.

FIG. 19 shows the synthetic single beam spectrum [F] of the sample gas. This was obtained by conducting a Fourier transformation on the interferogram [B] of the sample gas with a lowered point number and a lowered resolution. As compared with FIG. 18, there disappears (in the vicinity of 1,500 cm$^{-1}$) a signal of carbon dioxide and water which are the trace components (impurity).

Figure 20:
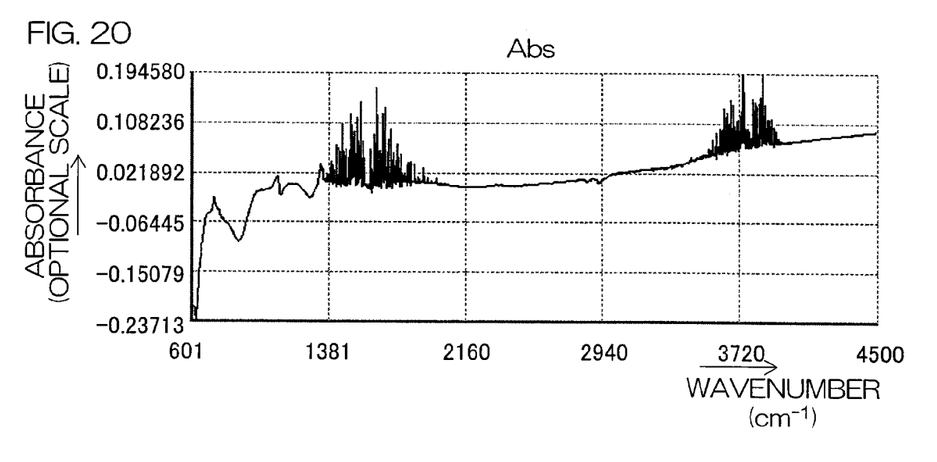
FIG. 20 shows a graph illustrating the normal absorbance spectrum of the sample gas according to Example 2.

FIG. 20 shows a graph of the normal absorbance spectrum Abs of the sample gas. The data in this graph were obtained by calculating the data of the graph [C] in FIG. 16 and the data of the graph [E] in FIG. 18. According to the graph, the average or DC component of the normal absorbance spectra Abs varies along the axis of abscissa. Thus, a drift influence is remarkably observed.

Figure 21:
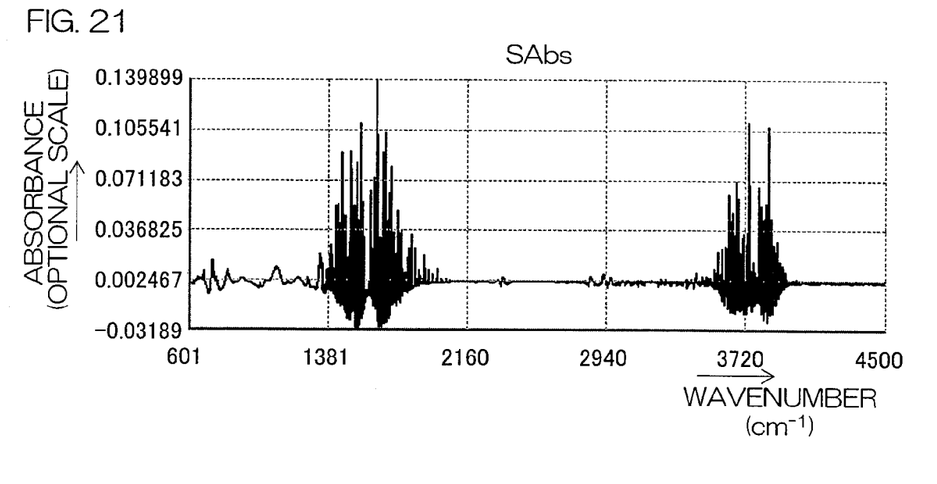
FIG. 21 shows a graph illustrating the synthetic absorbance spectrum of the sample gas according to Example 2.

FIG. 21 shows a graph of the synthetic absorbance spectrum SAbs of the sample gas. This is the absorbance spectrum obtained by calculating the data of the graph [E] in FIG. 18 and the data of the graph [F] in FIG. 19 with the use of synthetic background. As compared with FIG. 20, the average or DC component of the normal absorbance spectrum Abs does not vary along the axis of abscissa. Thus, a drift influence is offset.

Figure 22:
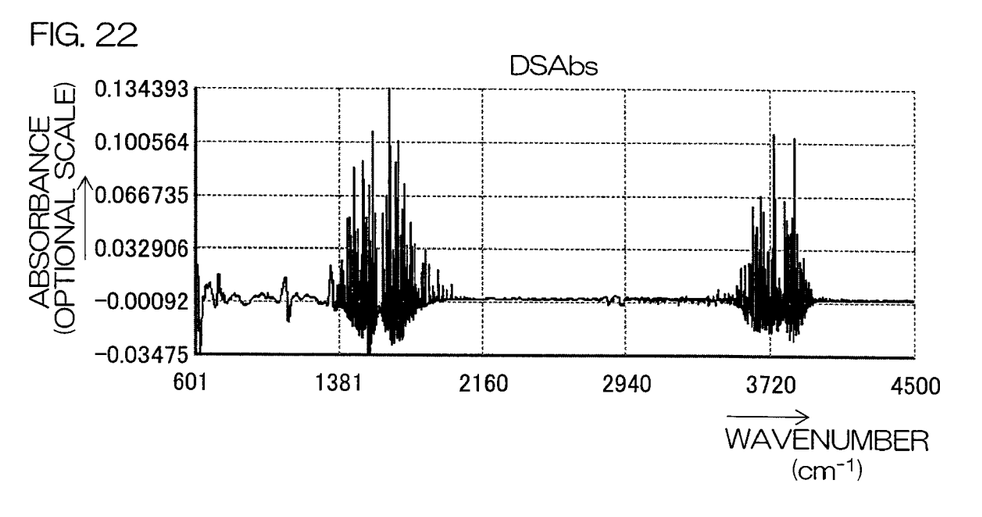
FIG. 22 shows a graph illustrating the double synthetic absorbance spectrum of the sample gas according to Example 2.

FIG. 22 shows a graph of the double synthetic absorbance spectrum DSAbs of the sample gas. This was obtained by calculating the data of the graph [C] in FIG. 16, the data of the graph [D] in FIG. 17, the data of the graph [E] in FIG. 18 and the data of the graph [F] in FIG. 19. Comparison with the graph in FIG. 21 confirms that the noise is lowered by conducting a calibration with the background gas.

The present application corresponds to Japanese Patent Application No. 2007-072738 filed with Japanese Patent Office on Mar. 20, 2007, and the whole disclosure thereof is incorporated herein by reference.

What is claimed is:

1. A gas concentration quantitative analysis method for quantitatively obtaining a concentration of a trace component contained in a sample gas with use of an FTIR (Fourier transform infrared spectrophotometer), the concentration being unknown, the method comprising the steps of:

specifying a sample gas and a measurement wavenumber region thereof;

specifying a background gas which is not absorbed in said measurement wavenumber region;

conducting an FTIR measurement of said background gas to obtain a single beam spectrum SB(BG) and a synthetic single beam spectrum SSB(BG);

conducting an FTIR measurement of said sample gas to obtain a single beam spectrum SB(Samp) and a synthetic single beam spectrum SSB(Samp);

calculating a double synthetic absorbance spectrum DSAbs of said sample gas as expressed by the following formula:

DSAbs=−log [SB(Samp)SSB(BG)/SSB(Samp)SB(BG)]

according to the single beam spectrum SB(BG) of said background gas, the synthetic single beam spectrum SSB(BG) of said background gas, the single beam spectrum SB(Samp) of said sample gas and the synthetic single beam spectrum SSB(Samp) of said sample gas; and obtaining the concentration of a trace component contained in said sample gas according to said double synthetic absorbance spectrum.

2. The gas concentration quantitative analysis method according to claim 1, further comprising the steps of:

calculating a normal absorbance spectrum Abs of said sample gas as expressed by the following formula:

Abs=−log SB(Samp)/SB(BG)

according to the single beam spectrum SB (Samp) of said sample gas and the single beam spectrum SB(BG) of said background gas;

obtaining the concentration of a trace component contained in said sample gas according to said normal absorbance spectrum.

3. The gas concentration quantitative analysis method according to claim 1, further comprising the steps of:

calculating a synthetic absorbance spectrum SAbs of said sample gas as expressed by the following formula:

SAbs=−log SB(Samp)/SSB(Samp)

according to the single beam spectrum SB(Samp) of said sample gas and the synthetic single beam spectrum SSB(Samp) of said sample gas;

obtaining the concentration of a trace component contained in said sample gas according to said synthetic absorbance spectrum.

4. The gas concentration quantitative analysis method according to claim 1, further comprising the steps of:

calculating a normal absorbance spectrum Abs of said sample gas as expressed by the following formula:

Abs=−log SB(Samp)/SB(BG)

according to the single beam spectrum SB(Samp) of said sample gas and the single beam spectrum SB(BG) of said background gas;

obtaining the concentration of a trace component in said sample gas according to said normal absorbance spectrum;

calculating, a synthetic absorbance spectrum SAbs of said sample gas as expressed by the following formula:

SAbs=−log SB(Samp)/SSB(Samp)

according to the single beam spectrum SB (Samp) of said sample gas and the synthetic single beam spectrum SSB (Samp) of said sample gas; and obtaining the concentration of the trace component in said sample gas according to said synthetic absorbance spectrum.

5. The gas concentration quantitative analysis method according to claim 1, wherein the step of obtaining the concentration of a trace component in said sample gas according to said double synthetic absorbance spectrum comprises a procedure of applying said double synthetic absorbance spectrum to a calibration curve that is data to determine a relationship between an integration values in said measurement wavenumber region of the absorbance spectrum of gas having a known concentration of a trace component, and the concentration of said trace component.

6. A gas concentration quantitative analysis apparatus for quantitatively obtaining a concentration of a trace component contained in a sample gas with use of an FTIR, said concentration being unknown, the apparatus comprising:

an FTIR measuring apparatus;

a unit arranged to specify a sample gas and a measurement wavenumber region thereof;

a unit arranged to specify a background gas which is not absorbed in said measurement wavenumber region;

a unit to conduct an FTIR measurement of said background gas to obtain a single beam spectrum SB(BG) and a synthetic single beam spectrum SSB(BG);

a unit arranged to conduct an FTIR measurement of said sample gas to obtain a single beam spectrum SB(Samp) and a synthetic single beam spectrum SSB(Samp);

a unit arranged to calculate a double synthetic absorbance spectrum DSAbs of said sample gas as expressed by the following formula:

DSAbs=−log [SB(Samp) SSB(BG)/SSB(Samp) SB(BG)]

according to the single beam spectrum SB(BG) of said background gas, the synthetic single beam spectrum SSB(BG) of said background gas, the single beam spectrum SB(Samp) of said sample gas and the synthetic single beam spectrum SSB(Samp) of said sample gas; and a unit arranged to obtain the concentration of a trace component contained in said sample gas according to said double synthetic absorbance spectrum.

7. The gas concentration quantitative analysis apparatus according to claim 6, wherein said unit arranged to obtain the concentration of a trace component in said sample gas is arranged to apply said double synthetic absorbance spectrum to a calibration curve that is data to determine a relationship between an integration values in said measurement wavenumber region of the absorbance spectrum of gas having a known concentration of a trace component, and the concentration of said trace component.

* * * * *